United States Patent [19]

Kim et al.

[11] 4,352,753
[45] Oct. 5, 1982

[54] 3-[[(2,3-DIHYDRO-1H-INDOL-2-yl)CARBONYL]THIO]PROPANOIC (AND ACETIC) ACIDS AS INTERMEDIATES

[75] Inventors: Dong H. Kim, Wayne; Ronald J. McCaully, Malvern, both of Pa.

[73] Assignee: American Home Products Corporation, New York, N.Y.

[21] Appl. No.: 220,652

[22] Filed: Dec. 29, 1980

[30] Foreign Application Priority Data

Aug. 11, 1980 [AR] Argentina .............................. 282109

[51] Int. Cl.³ .................. C07D 209/12; C07D 209/18
[52] U.S. Cl. ................. 260/326.12 R; 260/326.11 R; 260/326.13 C; 260/326.13 D; 424/274
[58] Field of Search .................. 260/326.14 R, 326.12, 260/326.13, 326.11 R; 424/258, 274

[56] References Cited

U.S. PATENT DOCUMENTS

| | | | |
|---|---|---|---|
| 3,465,042 | 9/1969 | Hardtmann et al. | 260/591 |
| 3,689,503 | 9/1972 | Reynolds et al. | 260/326.13 |
| 3,867,374 | 2/1975 | Reynolds et al. | 260/239.3 |
| 4,046,889 | 9/1977 | Ondetti et al. | 424/244 |
| 4,105,776 | 8/1978 | Ondetti et al. | 424/274 |
| 4,192,945 | 3/1980 | Ondetti | 546/245 |
| 4,199,512 | 4/1980 | Ondetti | 260/326.12 |
| 4,225,495 | 9/1980 | Ondetti | 260/244.4 |
| 4,251,444 | 2/1981 | Freed et al. | 260/244.4 |
| 4,256,751 | 3/1981 | Hayashi et al. | 424/258 |
| 4,303,583 | 12/1981 | Kim et al. | 260/239.3 |

OTHER PUBLICATIONS

Cheung, Hong-Son et al., "Binding of Peptide . . . " etc., *J. Biol. Chem.* 255, pp. 401–407, (1980).

Hastan, E., "Protection of Carboxy Groups", *Protective Groups in Organic Chemistry*, (McOmie, editor), pp. 183–185, (1973).

John H. Laragh, "The Renin System in High Blood Pressure, From Disbelief to Reality, etc.", Prog. in Cardio. Vasc. Disease, XXI, No. 3, pp. 159–166, (Nov./Dec., 1978).

Cushman et al., "Design of New Antihypertensive Drugs, etc.", Prog. in Cardio. Vasc. Disease, XXI, No. 3, pp. 176–182, (Nov./Dec., 1978).

*Primary Examiner*—Donald G. Daus
*Assistant Examiner*—G. Hendricks
*Attorney, Agent, or Firm*—Arthur G. Seifert

[57] ABSTRACT

Disclosed herein are 3[[(2,3-dihydro-1H-indole-2-yl)carbonyl]thio]propanoic (and acetic) acids of the general formula:

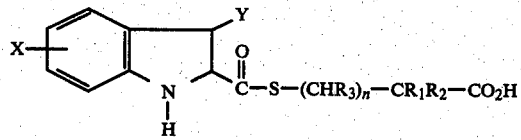

wherein:

n is 1 or 0;

$R_1$ is hydrogen, lower alkyl, aryl, or aralkyl;

$R_2$ is hydrogen or lower alkyl;

$R_3$ is hydrogen, lower alkyl or aroyl;

X is hydrogen, hydroxy, lower alkyl, lower alkoxy, or halogen; and

Y is hydrogen, lower alkyl, or aryl; or salts thereof.

These compounds are intermediates for the production of 1H,3H-[1,4]thiazepino[4,3-a]indoles and 1H-[1,4]thiazino[4,3-a]indoles which possess Angiotensin Converting Enzyme inhibition activity and anti-hypertensive activity.

10 Claims, No Drawings

3-[[(2,3-DIHYDRO-1H-INDOL-2-yl)CARBONYL]-THIO]PROPANOIC (AND ACETIC) ACIDS AS INTERMEDIATES

CROSS-REFERENCE TO RELATED APPLICATIONS

The 3-[[(2,3-dihydro-1H-indole-2-yl)carbonyl]thio]propanoic (and acetic) acids of this invention are novel intermediates for the production of 1H,3H-[1,4]thiazepino[4,3-a]indoles and 1H-[1,4]thiazino[4,3-a]indoles which are described and claimed in copending applications Ser. No. 65,817, filed Aug. 13, 1979, and Ser. No. 164,992, filed July 1, 1980, now U.S. Pat. No. 4,303,583.

SUMMARY OF THE INVENTION

This invention concerns 3-[[(2,3-dihydro-1H-indol-2-yl)carbonyl]thio]propanoic (and acetic) acids of the general formula:

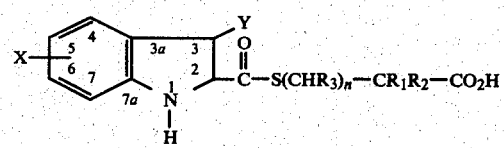

I wherein n, X, Y, $R_1$, $R_2$ and $R_3$ are defined below. Precursors of the compounds of Formula I include those in which either or both the indole nitrogen or the carboxylic acid are protected. The compounds of Formula I and the protected precursors, or salts thereof, are useful in the production of 1H,3H-[1,4]thiazepino[4,3-a]indoles and 1H-[1,4]thiazino[4,3-a]indoles having the formula:

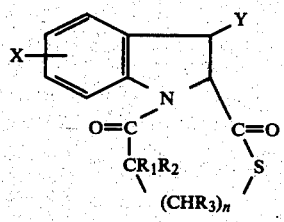

II wherein:

n is 1 or 0;

$R_1$ is hydrogen, lower alkyl, aryl, or aralkyl;

$R_2$ is hydrogen or lower alkyl;

$R_3$ is hydrogen, lower alkyl or aroyl;

$R_5$ is hydroxy, amino, or lower alkoxy;

X is hydrogen, hydroxy, lower alkyl, lower alkoxy, or halogen; and

Y is hydrogen, lower alkyl, or aryl.

The compounds of Formula II act as inhibitors of angiotensin converting enzyme (ACE) and are useful as agents for the treatment of hypertension and for the study of the renin-angiotensin-aldosterone system of warm-blooded animals.

As used herein, "lower alkyl" and "lower alkoxy" refer to groups having up to 4 carbon atoms. "Aryl" refers to phenyl or phenyl substituted by a halogen, lower alkyl, or lower alkoxy group.

"Aralkyl" refers to benzyl or benzyl substituted as above for phenyl. "Aroyl" refers to benzoyl or benzoyl substituted as above for phenyl. "Halogen" refers to chlorine, bromine and fluorine.

BACKGROUND OF THE INVENTION

In pharmacological research on hypertension, recent attention has focused on the study of the renin-angiotensin-aldosterone system, and, in particular, on the development of an effective anti-hypertensive agent which would, theoretically, achieve its result by inhibiting the action of angiotensin converting enzyme in converting angiotensin I to angiotensin II. The inhibition of the production of angiotensin II became important because of the discoveries that angiotensin II is the most potent pressor agent (vasoconstrictor) present in the mammalian body and, in addition, stimulates the adrenal cortex to release aldosterone, thereby causing excessive sodium retention and fluid retention, contributing further to the hypertensive state. Thus, inhibiting the conversion of angiotensin I to angiotensin II is believed to work directly on the primary biochemical mechanisms creating increased blood pressure. For a description of the mechanisms and of the mammalian renal-angiotensin-aldosterone system, see John H. Laragh, "The Renin System in High Blood Pressure, From Disbelief to Reality: Converting-Enzyme Blockade for Analysis and Treatment", Prog. in Cardio. Vasc. Disease, XXI, No. 3, 159–166 (November, 1978).

Recently, a series of proline derivatives has been found to act an inhibitors of angiotensin converting enzyme and as antihypertensive agents. Of these proline derivatives, D-3-mercapto-2-methylpropanoyl-L-proline has been reported to be the most effective, including being effective when administered orally. These proline and mercaptoproline derivatives and various pharmacological test results thereon are described in Cushman et al., "Design of New Anti-hypertensive Drugs: Potent and Specific Inhibitors of Angiotension Converting Enzyme", Prog. in Cardio. Diseases, Vol. XXI, No. 3 (Nov./Dec., 1978), and in U.S. Pat. Nos. 4,046,889 and 4,105,776, both to Ondetti and Cushman. Additionally, U.S. Pat. No. 4,225,495 to Ondetti discloses various hexahydro-1H,5H-pyrrolo[2,1-c][1,4]thiazepine-1,5-diones and tetrahydro-1H-pyrrolo[2,1-c][1,4]thiazine-1,4(3H)-diones as hypotensive agents. U.S. Pat. No. 4,225,495 also discloses 3-[L-prolylthio]-2-methylpropanoic acid and related compounds as intermediates for the production of said thiazepines and thiazines.

DETAILED DESCRIPTION OF THE INVENTION

The generic description of the invention is given by Formulas I and II. A preferred group of compounds of Formulas I and II are those in which $R_3$ is hydrogen or lower alkyl. Further preferred compounds of Formulas I and II include those in which Y is hydrogen or lower alkyl; $R_1$ is hydrogen; and n is 1 and $R_2$ is hydrogen. Particularly preferred compounds of Formulas I and II include those in which X is hydrogen; Y is hydrogen; $R_1$ is lower alkyl; n is 1, $R_1$ is lower alkyl, and $R_2$ and $R_3$ are hydrogen; n is 0, $R_1$ is lower alkyl, and $R_2$ is hydrogen; and $R_1$ is methyl.

Where either Y or $R_3$ of Formula I or II is other than hydrogen, the carbon atom to which it is attached is an asymmetric carbon atom. Similarly, where $R_1$ and $R_2$ are different, the carbon atom to which they are attached is an asymmetric carbon atom. Additionally, the carbon atom designated 2 in Formula I and the carbon atom designated 11a in Formula IIa below and the carbon atom designated 10a in Formula IIb below are asymmetric.

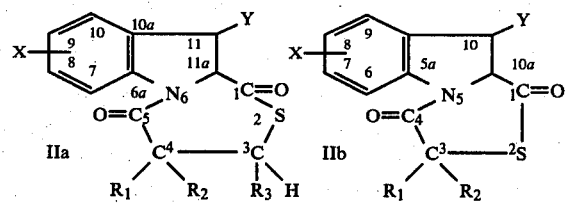

Thus, the compounds of the invention (including intermediate compounds) exist in stereoisomeric forms or in racemic mixtures thereof, all of which are within the scope of the invention. When Y is hydrogen in Formulas IIa and IIb, the 11aS and 10aS isomers are preferred. When Y is hydrogen in Formula I, the 2S isomer is preferred.

The following compounds of Formula IIa are preferred: The compounds in which X, Y, $R_2$ and $R_3$ are hydrogen and $R_1$ is methyl, which is 3,4,11,11a-tetrahydro-4-methyl-1$\underline{H}$,5$\underline{H}$-[1,4]thiazepino[4,3-a]indole-1,5-dione; and the compound in which X, Y, $R_1$, $R_2$, and $R_3$ are hydrogen, which is 3,4,11,11a-tetrahydro-1$\underline{H}$,5$\underline{H}$[1,4]thiazepino[4,3-a]indole-1,5-dione. Preferred stereoisomers of the 4-methyl compound are the 11aS,4S and 11aS,4R isomers.

The following compounds of Formula IIb are preferred: The compound in which X, Y, and $R_2$ are hydrogen and $R_1$ is methyl, which is 10,10a-dihydro-3-methyl-1$\underline{H}$-[1,4]thiazino[4,3-a]indole-1,4-(3$\underline{H}$)-dione; and the compound in which X, Y, $R_1$, and $R_2$ are hydrogen, which is 10,10a-dihydro-1$\underline{H}$[1,4]thiazino[4,3-a]indole-1,4(3$\underline{H}$)-dione.

The thiolactones of Formula II are prepared by cyclizing a compound of the Formula I:

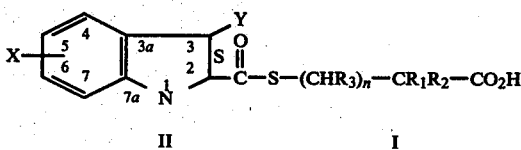

wherein n, $R_1$, $R_2$, $R_3$, X and Y are as defined above. The following reaction sequence is utilized to form the intermediate of Formula I:

(a) The free carboxylic acid of a (S-protected) thiol carboxylic acid of the formula GS(CHR$_3$)$_n$—CR$_1$R$_2$CO$_2$H, wherein G is a thiol protecting group and n, $R_1$, $R_2$ and $R_3$ are as previously defined, is protected with a carboxylic acid protecting group (Z);

(b) The thiol protecting group G is removed;

(c) The resulting thiol is reacted with an (N-protected)-2,3-dihydro-indole carboxylic acid of the formula:

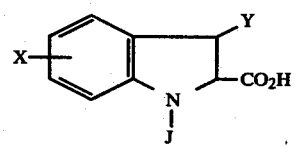

wherein J is an amino protecting group and X and Y are as previously defined, to form a compound of Formula I in which the carboxylic acid and the amine are both protected;

(d) removing said carboxylic acid and amino protecting groups.

The cyclization of the unprotected intermediate I to form the thiolactone products of Formula II can be achieved by any of many coupling reagents which are used in the peptide synthesis. Dicyclihexylcarbodiimide (DCC) is a typical and preferred reagent for this peptide cyclization. An addition of a small amount of 4-dimethylaminopyridine which acts as a catalyst in the reaction is recommended. Other reagents and reaction conditions which are useful for peptide bond coupling reactions can be found in Bodanszky et al., Peptide Synthesis, pp. 116–121 (John Wiley and Sons, 1976).

The (S-protected) thiol-carboxylic acid starting material of step a above may be a commercially available product or may be made from readily available reagents by methods well-known to those skilled in the art of organic chemistry. G, the thiol-protecting group may be a known sulfhydryl protecting group such as the acetyl, benzoyl, or substituted benzoyl (e.g. p-nitrobenzoyl)thioester groups; or a thioether formed with a benzyl group. The reagents and methods of forming such (S-protected) thiol-carboxylic acids are known to those skilled in the art. The thiol protecting group chosen should not be removable by such conditions that the carboxylic acid protecting group is also removed. Such thioester protecting groups may be removed (deprotection of step b) by treatment with an ammonia-methanol solution, aqueous ammonia solution, or sodium methoxide in methanol solution. The preparation and removal of thioether and thioester protecting groups is described in Chapter 7 of McOmie, J. F. W., ed., Protective Groups in Organic Chemistry, Plenum Press (1973) at pages 241-270 and 286-295, respectively. The acetyl protecting group is preferred and the methanolic ammonia solution is the preferred reagent for deprotection of said sulfhydryl group (step b).

The carboxylic acid protecting group, Z, may be a t-butyl group; a substituted benzyl group, such as a p-methoxybenzyl or a 2,4,6-trimethyl benzyl group; or a benzhydryl group. The t-butyl group is preferred. The removable carboxylic acid protecting group utilized, preferably, should be removable under the same conditions by which the secondary amino protecting group J is removable, but should not be removable under the conditions used to remove the thiol protecting group G.

The esterification of the (S-protected) thiol-carboxylic acid with a t-butyl group may be accomplished by reacting them with t-butyl alcohol in an inert solvent, such as chloroform or dioxane, in the presence of a condensation agent such as dicyclohexylcarbodiimide; or by reacting them with isobutylene in methylene chloride in the presence of an acid catalyst such as sulfuric acid. The latter method is preferred.

The benzyl and substituted benzyl esters may be formed by reacting the acid with the appropriate benzyl alcohol in an inert solvent, such as benzene in the presence of an acid catalyst, such as sulfuric acid.

The t-butyl, benzyl and substituted benzyl groups are preferably removed using trifluoroacetic acid at from 0° C. to room temperatures (25° C.). Other methods of removing and forming the carboxylic acid protecting group Z are well-known to those skilled in the organic chemistry. Such methods and reagents, as well as other suitable carboxylic acid protecting groups, are described in McOmie, supra, Chapter 5, particularly pages 196–197 with respect to the t-butyl and benzyl or substituted benzyl esters and table 5.1.

With respect to preparation step c, suitable amino protecting groups, J, may be chosen from the urethane-type amino protecting groups such as those described in Table 4 of M. Bodanszky et al., *Peptide Synthesis*, pp. 35-7 (John Wiley and Sons, 1976). Preferred are such urethane type protecting groups which are removable by treatment with trifluoroacetic acid (TFA). Examples of such protecting groups are t-butyloxycarbonyl (Boc), 2-(p-biphenyl)isopropyloxycarbonyl (Bpoc) and benzyl or substituted benzyloxycarbonyl (e.g. p-methoxybenzyloxycarbonyl) groups. Boc may be introduced by reacting di-t-butyldicarbonate with the appropriate substituted 2,3-dihydro-indole carboxylic acid. Other methods of introducing and of removing Boc and other amino protecting groups are well-known in the peptide and penicillin arts and are described in, for example, Bodanszky, et al., supra, pp. 18–49.

The formation of the thioester from the N-protected-2,3-dihydro-indole carboxylic acid and mercaptoalkylcarboxylic acid which is protected at the carboxylic acid end (process step c) can be accomplished by a coupling reagent used widely in the peptide synthesis, such as dicyclihexylcarbodiimide (DCC) or N-ethyl-N'-(3-dimethylaminopropyl)carbodiimide and related reagents. Example of such reagents are found in pp. 116–121 "Peptide Synthesis" (2nd Ed.) by M. Bodanszky, Y. S. Klausner, and M. A. Ondetti, Wiley Interscience Publication, New York (1976). The presence of small amounts of 4-dimethylaminopyridine is used to accelerate the reaction and increase the yield. The preferred reagent for the reaction is DCC in the presence of 4-dimethylaminopyridine used at room temperature for several hours in a methylene chloride medium.

The same thioester can also be prepared by treatment of the reactants with diethyl phosphocyanidate (DEPC) or diphenyl phosphorazidate (DPPA) in dimethylformamide in the presence of triethylamine [Yamada et al., J. Org. Chem., 39, 3302 (1974)], or by means of carbonyldiimidazole or carbonyl-di-1,2,4-triazole [Gais, Angew, Chem. Int. Edit. Engl., 16, 244 (1977)].

As previously noted, removal of both the amino and carboxylic acid protecting groups (J and Z) from the protected intermediate V (i.e. step d) is preferably accomplished using the same reagent in one step. This is the reason for selecting protecting groups J and Z which may be cleaved under the same treatment, for example, using the preferred trifluoroacetic acid treatment. It will be obvious to those skilled in the art that this deprotection may be accomplished using more than one step or more than one cleaving agent, depending upon which J and Z protecting groups were chosen for the particular synthesis. The methods and conditions for such deprotection reactions are known to those skilled in the penicillin and peptide arts.

An alternate method of making the compounds of Formula II of the invention utilizes a thioester cyclization of the mercapto compounds of Formula IV shown below.

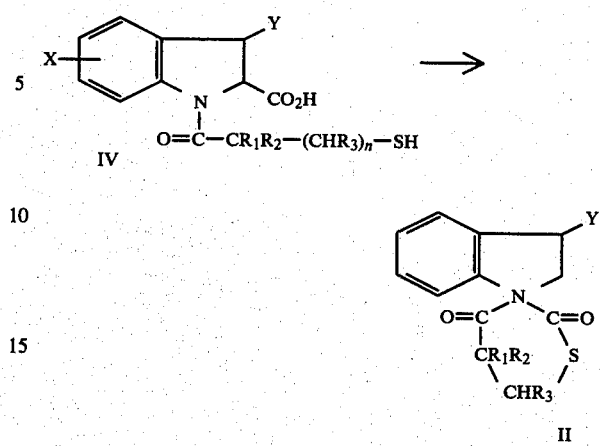

where the n, X, Y, $R_1$, $R_2$ and $R_3$ substituents are as previously defined.

The formation of these thiolactones (i.e. the 1$\underline{H}$,3$\underline{H}$-[1,4]thiazepino[4,3-a]indoles and 1-$\underline{H}$-[1,4]thiazino[4,3-a]indoles of Formula II) can be accomplished by a coupling reagent used widely in the peptide synthesis, such as dicyclohexylcarbodiimide (DCC) or N-ethyl-N'-(3-dimethylaminopropyl)carbodiimide and related reagents. Example of such reagents are found in pp. 116–121 "Peptide Synthesis" (2nd Ed.) by M. Bodanszky, Y. S. Klausner, and M. A. Ondetti, Wiley Interscience Publication, New York (1976). The presence of small amounts of 4-dimethylaminopyridine is used to accelerate the reaction and increase the yield. The preferred reagent for the reaction is DCC in the presence of 4-dimethylaminopyridine used at room temperature for several hours in a methylene chloride medium. The same thioester cyclizations can be accomplished by treatment of the reactants with diethyl phosphocyanidate (DEPC) or diphenyl phosphorazidate (DPPA) in dimethylformamide in the presence of triethylamine [Yamada et al., J. Org. Chem., 39, 3302 (1974)], or by means of carbonyldiimidazole or carbonyl-di-1, 2,4-triazole [Gais, Angew, Chem. Int. Edit. Engl., 16, 244 (1977)].

The mercapto compounds of Formula IV may be made from the corresponding thioacyl compounds by hydrolysis or ammonolysis. Such ammonolysis may be accomplished by first treating the appropriate thioacyl compound with a methanolic ammonia solution and thereafter treating the resulting product with acid, such as HCl, to a pH of about 2. The terminal thioacyl group would have the formula $-S-CO-R_8$ wherein $R_8$ is hydrogen, lower alkyl, aryl, or aralkyl. The acetylthio and benzoylthio groups are preferred terminal thioacyl groups.

The thioacyl intermediates just described are, in turn, made by coupling the desired thio-acid or thiol to an intermediate of Formulas V or VI below:

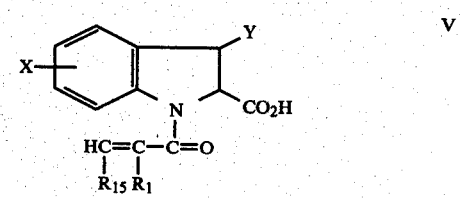

-continued

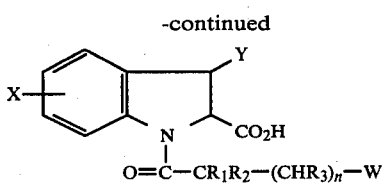

where n, X, Y, $R_1$, $R_2$ and $R_3$ are as previously defined; $R_{15}$ is hydrogen or lower alkyl; and W is bromine, chlorine, or iodine.

The intermediates of Formula V may be made by reacting an appropriately substituted (i.e. X and Y) 2,3-dihydro-indole, 2-carboxylic acid, in which the carboxylic acid is protected with an acryloyl of the formula $R_{15}HC=CR_1COR_{16}$ (VII) wherein $R_1$ and $R_{15}$ are as defined above and $COR_{16}$ is an activated carboxyl group such as an acyl halide, an active ester, or mixed anhydride. The acyl halide group is preferred. This reaction is run in an inert organic solvent, such as ether or methylene chloride, in the presence of an acid scavenger, such as triethylamine, where an acid is formed during the reaction.

In order to make an intermediate of Formula VI, a substituted alkyl acyl compound of the formula $W(CHR_3)_n CR_1R_2COR_{16}$ (VIII) wherein x, W, $R_1$, $R_2$, $R_3$, and $COR_{16}$ are as previously defined, may be reacted with 2,3-dihydro-indole, 2-carboxylic acid. In this procedure, the carboxylic acid group need not be protected.

The preparation of the 2,3-dihydro-indole, 2-carboxylic acid starting material is described by Corey et al., J. Am. Chem. Soc., 92, 2476–2488 (1970). The desired X and Y substituents may be obtained on such starting material in a manner known to those skilled in the art.

The carboxylic acid protecting group used in forming intermediate V may be chosen from any known carboxylic acid protecting, for example, methyl, ethyl, and t-butyl esters and various amide groups. Various carboxylic acid protecting groups and their use are described in McOmie, ed., *Protective Groups in Organic Chemistry*, Chapter 5 (Plenum Press, 1973). An appropriate protective group should be selected on the basis that (1) the reagent by which it is introduced does not react with another part of the molecule; (2) the protective group does not interfere with subsequent reactions; and (3) the process by which it is removed does not effect other portions of the molecule.

The compounds of Formula I form basic salts with various inorganic and organic bases which are also within the scope of the invention. Such salts include ammonium salts, alkali metal salts like sodium and potassium salts, alkaline earth metal salts like the calcium and magnesium salts, salts with organic bases, e.g. dicyclohexylamine salt, benzathine, N-methyl-D-glucamine, hydrabamine salts, salts with amino acids like arginine, lysine and the like. Such salts may be formed separately or they may be formed in isolating or purifying the product.

The compounds of Formula I may also form acidic salts with various inorganic and organic acids, for example hydrochloric acid, trifluoroacetic acid, methanesulfonic acid (mesylate), and toluenesulfonic acid (tosylate). Such acidic salts are also within the scope of the invention, and may similarly be formed separately or during the workup of the product.

The angiotensin converting enzyme (ACE) inhibitory property of the compounds of Formula II is measured in vitro and in vivo. The in vitro assay utilizes rabbit lung extract and a specific tripeptide substrate, hippuryl-L-histidyl-L-leucine being preferred, and follows the method of Cushman et al., Biochem. Pharmacol., 20, 1637–1648 (1971).

The in vivo ACE inhibitory activity of the compounds is measured according to the procedure described in Rubin et al., J. Pharmacol. Exp. Ther., 204, 271–280 (1978), which utilizes the conscious normotensive rat as a subject. An angiotensin converting enzyme inhibitor would not be expected necessarily to lower arterial pressure in the normotensive rat, but would be expected to block angiotensin I pressor responses without grossly altering angiotensin II responses. Additionally, the vasodepressor response to bradykinin would be expected to be augmented since angiotensin converting enzyme is known to inactivate bradykinin normally.

The anti-hypertensive effect of the compounds of the invention is measured in the spontaneously hypertensive rat. In this procedure, systolic pressure of male spontaneously hypertensive rats is measured by an indirect technique using the Decker Caudal Plethysmograph or other appropriate sensor. Groups usually consist of 4 or more rats. Drugs are usually administered orally. Pressures are usually read prior to drug administration and at 1.5, 4 and 24 hours thereafter. This schedule may be altered depending upon the behavior of the drug. This procedure measures the hypotensive effect of the subject compounds in a hypertensive subject using a single dose and measuring the response over a 24 hour period. Angiotensin converting enzyme inhibitors when utilized as anti-hypertensive agents are most effective upon such extended administration and exhibit no significant side-effects when administered at moderate or low doses. As noted earlier, the compounds of the invention exhibit a hypotensive (depressor) response only when administered to hypertensive subjects and would not be expected to lower blood pressures significantly in normotensive subjects.

The compounds of Formula II may be administered orally, intravenously, intraperitoneally, intramuscularly, or subcutaneously. Oral administration is preferred.

When employed to lower blood pressures in hypertensive subjects the effective dosage of the compound being utilized for such treatment will vary according to the particular compound being employed, the severity and nature of condition being treated, and the particular subject being treated. Therapy should be initiated at lower doses (in mg/kg./day) in the effective range of a given compound, the dosage thereafter being increased, if necessary, to produce the desired anti-hypertensive effect.

Further, when employed as anti-hypertensive agents or as angiotensin converting enzyme inhibitors, the compounds of the invention may be administered alone or in combination with pharmaceutically acceptable carriers. The proportion and nature of such carriers would be determined by the solubility and other chemical properties of the compound selected, the chosen route of administration, and standard pharmaceutical practice.

A preferred compound of Formula I of the invention is the compound wherein n is 1; X, Y, $R_2$, and $R_3$ are hydrogen; and $R_1$ is methyl, which is 3-[[(2,3-dihydro-1H-indol-2-yl)-carbonyl]thio]-2-methyl-propanoic acid.

The indolinyl-2S and 2S-methyl isomers thereof are preferred. A preferred method of making such stereochemically preferred compounds involves starting with, for example, 3-benzoylthio-2S-methyl-propanoic acid or 3-acetylthio-2S-methyl-propanoic acid, protecting the carboxylic acid end, and then deprotecting the sulfur end. The resulting 3-thiol-2S-methyl-propanoic acid, t-butyl ester is reacted with, for example, racemic (at the 2-position) N-t-butyl-2,3-dihydro-indole-2-carboxylic acid and, thereafter, the desired diastereoisomer is isolated. The diastereoisomer may be isolated more conveniently in the protected form of the compound of Formula I and then converted.

What is claimed is:

1. A compound of the formula:

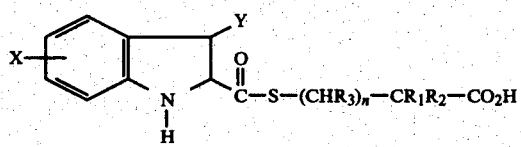

wherein:

n is 1 or 0;

$R_1$ is hydrogen, lower alkyl of 1 to 4 carbon atoms, phenyl, substituted phenyl, benzyl, or substituted benzyl;

$R_2$ is hydrogen or lower alkyl of 1 to 4 carbon atoms;

$R_3$ is hydrogen, lower alkyl of 1 to 4 carbon atoms, benzoyl, or substituted benzoyl;

X is hydrogen, hydroxy, lower alkyl of 1 to 4 carbon atoms, lower alkoxy of 1 to 4 carbon atoms, or halogen; and Y is hydrogen, lower alkyl of 1 to 4 carbon atoms, phenyl, or substituted phenyl;

or salts thereof;

wherein substituted phenyl, substituted benzyl and substituted benzoyl refer to such groups with the phenyl ring optionally substituted with a halogen, a lower alkyl group of 1 to 4 carbon atoms, or a lower alkoxy group of 1 to 4 carbon atoms.

2. A compound according to claim 1 in which $R_3$ is hydrogen or lower alkyl of 1 to 4 carbon atoms.

3. A compound according to claim 1 in which n is 1.

4. A compound according to claim 1 in which Y is hydrogen or lower alkyl of 1 to 4 carbon atoms.

5. A compound according to claim 1 in which $R_2$ and $R_3$ are hydrogen.

6. A compound according to claim 1 in which n is 1 and X, Y, $R_2$, and $R_3$ are hydrogen.

7. A compound according to claim 6 in which $R_1$ is hydrogen or lower alkyl of 1 to 4 carbon atoms.

8. A compound according to claim 1 in which n is 1; X, Y, $R_2$, and $R_3$ are hydrogen; and $R_1$ is methyl, which is 3-[[(2,3-dihydro-1H-indol-2-yl)carbonyl]thio]-2-methyl-propanoic acid.

9. A compound according to claim 8 which is the indolinyl-2S isomer.

10. A compound according to claim 8 which is the 2S-methyl isomer.

* * * * *